(12) United States Patent
Watson

(10) Patent No.: US 11,990,219 B1
(45) Date of Patent: May 21, 2024

(54) AUGMENTED THERAPY

(71) Applicant: Augment Therapy, LLC, Chagrin Falls, OH (US)

(72) Inventor: Lindsay Watson, Chagrin Falls, OH (US)

(73) Assignee: Augment Therapy, LLC, Chagrin Falls, OH (US)

( * ) Notice: Subject to any disclaimer, the term of this patent is extended or adjusted under 35 U.S.C. 154(b) by 837 days.

(21) Appl. No.: 16/400,471

(22) Filed: May 1, 2019

Related U.S. Application Data

(60) Provisional application No. 62/665,201, filed on May 1, 2018.

(51) Int. Cl.
| | |
|---|---|
| *G16H 20/30* | (2018.01) |
| *A61B 5/00* | (2006.01) |
| *A61B 5/11* | (2006.01) |
| *A63B 69/00* | (2006.01) |
| *G06F 16/78* | (2019.01) |
| *G09B 5/02* | (2006.01) |
| *G09B 5/06* | (2006.01) |
| *G09B 19/00* | (2006.01) |

(52) U.S. Cl.
CPC ........... *G16H 20/30* (2018.01); *A61B 5/1121* (2013.01); *A61B 5/744* (2013.01); *A63B 69/00* (2013.01); *G06F 16/78* (2019.01); *G09B 5/02* (2013.01); *A61B 5/1114* (2013.01); *A63B 2220/40* (2013.01); *A63B 2220/803* (2013.01); *G09B 5/065* (2013.01); *G09B 19/0038* (2013.01)

(58) Field of Classification Search
CPC .... G16H 20/30; A63B 69/00; A63B 2220/40; A63B 2220/803; A61B 5/1121; A61B 5/744; A61B 5/1114; G09B 5/02; G09B 5/065; G09B 19/0038
See application file for complete search history.

(56) References Cited

U.S. PATENT DOCUMENTS

| | | | |
|---|---|---|---|
| 9,844,730 B1* | 12/2017 | Dawson ................ | A63F 13/211 |
| 2009/0299232 A1 | 12/2009 | Lanfermann | |
| 2010/0022351 A1* | 1/2010 | Lanfermann ...... | A63B 24/0006 482/1 |
| 2010/0280418 A1* | 11/2010 | Klose .................... | A61B 5/744 600/595 |
| 2011/0098109 A1* | 4/2011 | Leake ................... | A63F 13/213 463/43 |
| 2012/0206577 A1* | 8/2012 | Guckenberger ..... | G09B 19/003 348/47 |

(Continued)

FOREIGN PATENT DOCUMENTS

EP    3122430 A1    2/2017

*Primary Examiner* — Jay Trent Liddle
*Assistant Examiner* — Alyssa N Brandley
(74) *Attorney, Agent, or Firm* — Calfee, Halter & Griswold, LLP

(57) ABSTRACT

Systems and methods for facilitating the completion of physical therapy through the application of augmented-reality training exercises are provided. In certain exemplary embodiments, a digital avatar is displayed to a user demonstrating various physical therapy movements. Video data may be received from one or more cameras to identify and capture movement from the user. Movement of the user may be analyzed to determine if the user has performed the movements as demonstrated by the digital avatar.

20 Claims, 4 Drawing Sheets

(56) References Cited

U.S. PATENT DOCUMENTS

| | | | |
|---|---|---|---|
| 2013/0171601 A1* | 7/2013 | Yuasa | G06V 40/23 |
| | | | 434/258 |
| 2013/0178960 A1* | 7/2013 | Sheehan | G16H 40/67 |
| | | | 700/91 |
| 2013/0205311 A1* | 8/2013 | Ramaswamy | H04N 21/44213 |
| | | | 725/9 |
| 2014/0147820 A1 | 5/2014 | Snow et al. | |
| 2014/0188009 A1* | 7/2014 | Lange | A61B 5/1127 |
| | | | 600/595 |
| 2015/0327794 A1 | 11/2015 | Rahman et al. | |
| 2016/0101321 A1 | 4/2016 | Aragones et al. | |
| 2016/0199693 A1* | 7/2016 | Vermilyea | A61B 5/1128 |
| | | | 700/91 |
| 2016/0239639 A1 | 8/2016 | Bernard-Paroly | |
| 2017/0103672 A1* | 4/2017 | Dey | G06F 3/011 |
| 2017/0354843 A1* | 12/2017 | Vuillerme | A61B 5/6898 |
| 2018/0228430 A1* | 8/2018 | Perez Marcos | A61B 5/225 |
| 2019/0295438 A1* | 9/2019 | Rubinstein | G09B 5/06 |

\* cited by examiner

AUGMENTED THERAPY

TECHNICAL FIELD

The present disclosure generally relates to facilitating the completion of physical therapy through the application of augmented-reality training exercises.

BACKGROUND

Physical therapy is a field which strives to encourage physical healing and improvement of function and reduction of pain through the incorporation of therapeutic exercise and by teaching patients how to manage their own symptoms. However, studies suggest that more than 70% of patients do not follow through with assigned exercises in a home setting and are discouraged by exercise in general regardless of the setting.

Visual feedback, mirror therapy, and obstacle engagement are among the therapeutic treatments which have been utilized to conduct therapies promoting complex motor coordination, proprioception, reduce phantom limb pain, and improve bilateral limb function for patients with hemiparesis or hemiplegia.

Mirror therapy involves the use of mirrors in front of a patient that is engaged in an exercise, providing feedback to the patient's brain for proprioception, coordination, and motor planning. Mirror therapy is typically used for patients that are recovering from a traumatic brain injury or stroke. The application of mirror images facilitates the brain's recognition of the paralytic side of the body which can facilitate neuromuscular memory and reintegration of neural pathways.

Other types of physical therapy have utilized physical obstacles and engagement devices within a patient's home-based, hospital-based and/or clinical environment to facilitate patient movement and exercise.

Therapeutic gaming has been used to combine the methods of visual feedback, mirror therapy, and obstacle engagement to create a more interactive therapy experience. Therapeutic gaming has been employed by physical therapists as a means to facilitate and engage patients to complete assigned exercises. Typically, therapeutic gaming platforms capture a patient's image and display the image back to the patient. The premise is that by converting the exercise to a visual experience, and by converting the patient's movements and image to a form visible to the patient, you can facilitate physical therapy performance similar to traditional mirror therapy.

In prior implementations of therapeutic gaming, simply taking video of the patient exercising and projecting their abstract image on the screen has not been effective in encouraging or engaging the patient enough to promote exercise or improve their exercise compliance. Previous implementations of therapeutic gaming have deviated from the traditional evidence-based exercise format and this has been found to negatively impact carryover to function. Carryover references the ability for a given exercise to have a positive impact on a patient's function, or general gross motor ability level in daily life. If exercises deviate too far away from the evidence-based exercise, the physical therapist may view the gaming software as fun, but ineffective in supporting patient progress and rehabilitation It is therefore appreciated that a need exists for an improved therapeutic gaming platform capable of further incentivizing therapy completion and collecting valuable patient data.

SUMMARY

In an exemplary embodiment, a method for facilitating the completion of an interactive physical therapy exercise is provided. The method comprises: receiving a video data stream from a first camera; analyzing the video data stream to identify at least one user; generating an avatar; displaying the avatar in at least one pose associated with a physical therapy exercise at a display, wherein the display is in proximity to the at least one user; prompting the at least one user to mimic the at least one pose; analyzing the video data stream to detect movement of the at least one user; determining if the at least one user successfully mimics the at least one pose based on the detected movement; and displaying a visual indicator when the at least one user successfully mimics the at least one pose.

In another exemplary embodiment, a system for facilitating the completion of an interactive physical therapy exercise is provided. The system comprises: a first camera configured to capture a video data stream; a processing unit configured to: receive the video data stream from the first camera; analyze the video data stream to identify at least one user; generate an avatar, wherein the avatar is operable to be displayed in at least one pose associated with a physical therapy exercise; generate a prompt to the at least one user to mimic the at least one pose; analyze the video data stream to detect movement of the at least one user; determine if the at least one user successfully mimics the at least one pose based on the detected movement; and generate a visual indicator when the at least one user successfully mimics the at least one pose.

In yet another exemplary embodiment, a method for facilitating the completion of an interactive physical therapy exercise is provided. The method comprises: receiving a video data stream from a first camera; analyzing the video data stream to identify at least one user; displaying an image of the at least one user based on the video stream; generating at least one digital object and displaying the digital object in proximity to the image of the at least one user; prompting the user to perform an interaction with the digital object; analyzing the video data stream to detect movement of the at least one user to determine if the user has performed the interaction; and, displaying a visual indicator when the at least one user successfully performs the interaction with the digital object.

These and other objects, features and advantages of the present disclosure will become apparent from the following detailed description of illustrative embodiments thereof, which is to be read in connection with the accompanying drawings.

BRIEF DESCRIPTION OF THE DRAWINGS

These and other features of the present disclosure will become better understood with regard to the following description and accompanying drawings in which.

DETAILED DESCRIPTION

Aspects and implementations of the present disclosure will be understood more fully from the detailed description given below and from the accompanying drawings of the various aspects and implementations of the disclosure. This should not be taken to limit the disclosure to the specific aspects or implementations, but explanation and understanding only.

Figure 1:
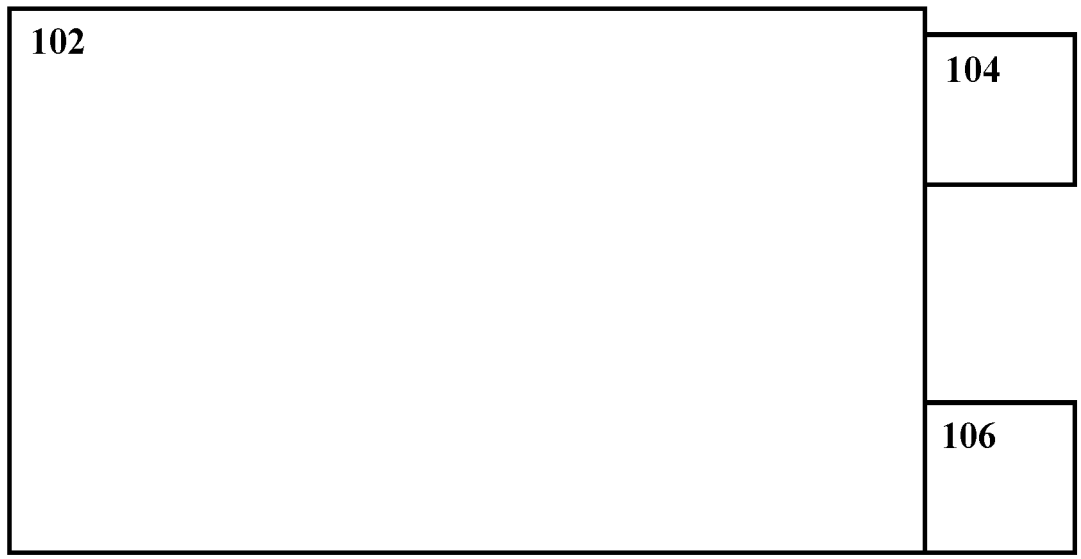
FIG. 1 shows an exemplary augmented therapy system.

FIG. 1 shows an exemplary augmented therapy system of the present disclosure. The System 100 comprises at least a Display 102, a Camera 104, and a Processing Unit 106. It is appreciated that the Display 102, Camera 104, and Processing Unit 106, may be configured as separate devices linked by a wireless or wired control signal, or integrated as a single device. It is further contemplated that System 100 may be comprised of additional technical elements configured to collect patient information including, but not limited to, a microphone, additional cameras, heart rate monitors, motion sensors, light detectors, etc.

Display 102 may comprise any digital display capable of displaying an image to a user or users such as, but not limited to a LCD, LED, OLED, monitor, television, cellular telephone, or tablet computer. Other compatible digital display configurations as will be appreciated by those of skill in the art. Display 102 may be a standalone device operable to receive input from a variety of input devices such as a computer, tablet, phone, etc., or may be integrated with an input device. In some embodiments, Display 102 is a configured to display 3D images or video which may be interpreted by a user with or without 3D glasses, or with or without additional hardware configured to assist in the interpretation of 3D image and video data. In certain embodiments, Display 102 may comprise additional displays, or one or more displays configured in a display array.

Camera 104 may comprise a single camera configured to capture image and video data in a single field of view, or, in come embodiments, may comprise a multi-camera array configured to capture image and video data in multiple directions or fields of view. Camera 104 is configured to record image and video data of a user and transmit said data to Processing Unit 106 for image processing. Camera 104 and Processing Unit 106 are further configured to interpret user movements based on the captured image and video data. In some embodiments, multiple users are monitored and have their movements interpreted by Camera 104 and Processing Unit 106. Tracking multiple users may be used to allow one user conduct the therapy session and lead or direct other users in specific movements. Tracking multiple users may also be used to introduce competitive goals that reward a user that finishes a task the fastest or with the highest degree of accuracy. In certain embodiments, Camera 104 and/or Processing Unit 106 may be configured to recognize certain movements automatically according to pre-programed settings. In certain embodiments, new gestures or movements may be added according to user need or preference. Processing Unit 106 is configured to transmit the captured image and video data for real-time, near real-time, or delayed display on Display 102. Camera 104 may also be configured to record said data on a computer storage for optional delayed playback or later analysis by Processing Unit 106.

Camera 104 may be affixed to Display 102 by a dock or holder. The dock or holder may be configured to be adjustable to accommodate multiple field of view adjustments, e.g. according to user preference. The dock or holder may be affixed to the Display 102 by clips, adhesive, screws, or other methods as will be apparent to those of skill in the art. It is further contemplated that Camera 104 may be configured to move about an axis secured to the Display 102 and track user movement as movement is made.

In some embodiments Camera 104 may be 3D depth sensing camera configured to gather image and video data. In some embodiments Camera 104 may be an infrared or thermographic camera. In other embodiments, Camera 104 is an Internet connected Webcam. In some embodiments Camera 104 may be connected to a storage device configured to record video data for delayed playback on Display 102. In other embodiments, Camera 104 is a tablet or cellular telephone. In some other embodiments Camera 104 is configured to determine heart rate by analyzing video data of a user. In yet another embodiment, Camera 104 may be configured to collect data on specific joints on the human body. Other types of data may also be determined based on the captured image and video data, such as, but not limited to, velocity of movement, range of motion, specific pediatric data such as single-limb stance, jumping in place, jumping forward, walking on a line, and gait analysis. It is further contemplated that frequency of use data, duration of exercise, and patient or therapist satisfaction data may also be collected. It will be appreciated that the discussed data may be captured by Camera 104 and interpreted at Processing Unit 106. Camera 104 and/or Processing Unit 106 may be embodied in or associated with an existing user device, e.g. a Microsoft XBOX with Kinect camera, Orbbec camera, Apple iPhone X camera, or the like. In some embodiments Camera 104 further comprises a processor and a memory, and may be configured to process data as is done in Processing Unit 106.

Processing Unit 106 may be configured to receive image and video data from Camera 104, augment said data in the form of a digital content overlay, e.g. generate a digital avatar, or other digital content, and transmit the augmented image and video data to Display 102 for display to a user. In some embodiments, a generated digital content overlay may generate objects or background images/scenes based on the received video data.

Processing Unit 106 comprises at least a processor in communication with a memory. The memory of Processing Unit 106 is configured to store instructions which can be executed by the processor. Processing Unit 106 may further comprise a storage device for long term storage of captured image and video data. The processor used in Processing Unit 106 may be a single core processor, a multi-core processor, or other processor configuration as appreciated in the art. The memory used in Processing Unit 106 may RAM, ROM, DRAM, SDRAM, DDR SDRAM, flash memory, or any other memory configuration operable to store instructions to be executed by the processor.

In some embodiments Processing Unit 106 has a user interface configured to allow user preferences to be applied to the data processing features of Processing Unit 106. For example, a therapist using System 100 may input a series of exercises or movements designed to test and obtain data points such as number of repetitions, range of motion, single-limb stance time, jump height, jump distance, hopping ability, ability to cross midline and in which quadrants and planes of movement, center of gravity, etc. These and other data points will be appreciated by those of skill in the art. The user interface of Processing Unit 106 is further configured to allow a user to set variable thresholds for said data points to establish completion metrics. These completion metrics may be different for each patient depending on their skill, age, height, weight, ability, etc., and therefore are customizable within the user interface. In some embodiments Processing Unit 106 is configured to collect said data points and transmit them to a patient's therapist, parent or guardian, or another responsible for monitoring a patient's therapy progress.

In some embodiments, the Camera 104 is configured to use a laser to project a grid array of light over the body of User 208 to detect the general body position and then places a virtual skeletal structure "over the body" to obtain the data points. The skeletal structure allocates joint positions which allow the user to interact with objects in the 3D world and place digital content in proximity to various parts of the User 208 body for interaction, such as catching fireflies and putting them in a bottle or kicking a virtual soccer ball.

It is appreciated that any of Display 102, Camera 104, and Processing Unit 106 may be configured in combination with another or similar devices configured to capture, store, display, or process image and video data.

Figure 2:
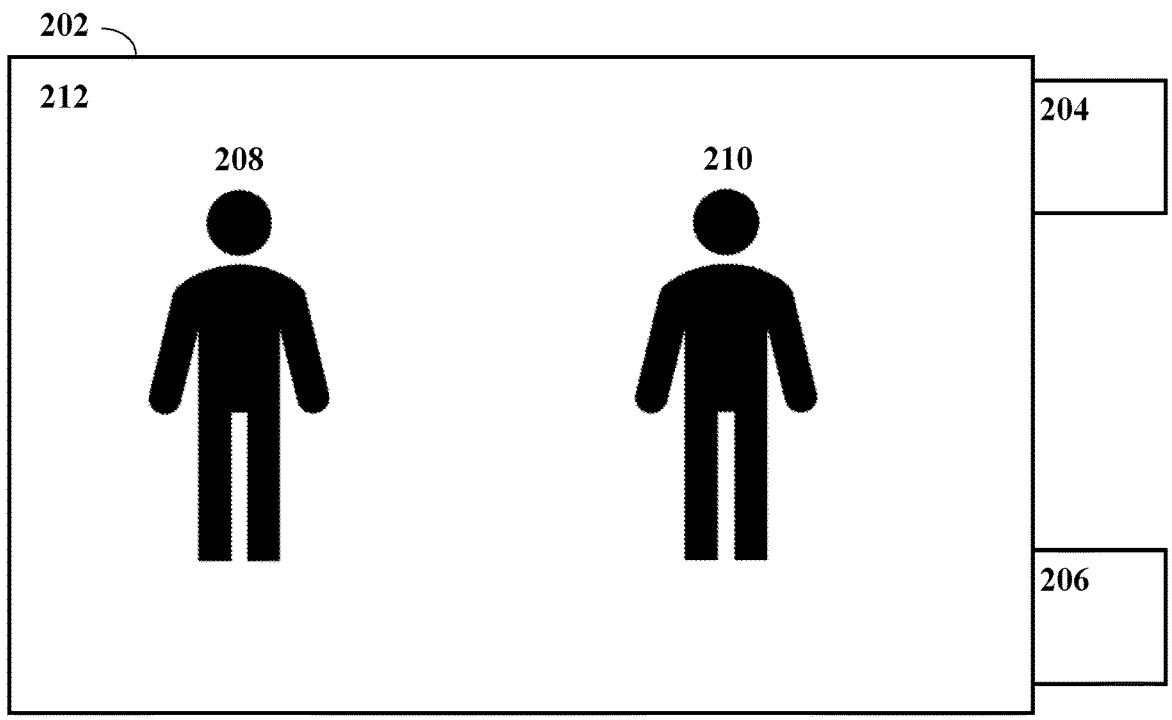
FIG. 2 shows an exemplary user interface for use with an exemplary augmented therapy system.

FIG. 2 is an exemplary user interface 200 for use with an exemplary augmented therapy system, e.g. System 100. Display 202, Camera 204, and Processing Device 206 may function in substantially the same way as the Display 102, Camera 104, and Processing Device 106 as previously described in reference to FIG. 1. In the exemplary user interface 200 of FIG. 2, a User 208 is represented by a digital image of the user. The digital image may be identical or nearly identical to the User 208, or, in some embodiments, may be a modified image of the user, e.g. a digital character. In some embodiments, the User 208 is represented by a digital image that has been augmented by an overlay of digital objects, i.e. a hat on the head, a parrot on the shoulder, etc.

The user interface 200 may further comprise Background 212. Background 212 may be real-time or near real-time image and video data of the surrounding environment of User 208. In some embodiments, Background 212 is an overlay of digital content, such as, but not limited to, e.g., space, jungle, city, or desert environments. Digital objects or environments may appear in Background 212 that User 208 is able to interact with. In certain embodiments, certain interactions may be prompted or instructed. For instance, a digital object such as a balloon may appear, and User 208 may reach out and move or pop the balloon. Other examples include grabbing fireflies to put into a jar or stomping on a launchpad to launch a rocket. Other digital environments are contemplated for customized therapeutic interaction such as a snow globe environment where the User 208 must jump up and down to make it snow and interact with the snow to make virtual snowballs. As digital objects or environments are overlaid onto background 212, they may remain in the background until User 208 interacts with them. Data and metrics surrounding the user interaction with the digital objects or environments may be sent to Processing Device 206 for processing. Optionally, real-time or near real-time feedback of user progress is displayed on Display 202. In some embodiments, Background 212 may change based on user movement. For example, as a User 208 makes walking motions, the image of the user will appear to traverse a digital environment of Background 212. In certain embodiments, the User 208 may be instructed or prompted to traverse the environment and interact with various obstacles along the way, e.g. an obstacle course.

In some embodiments, the User 208 is shown in real-time, while a digital Avatar 210 is also shown on the display. As the User 208 completes assigned tasks or goals, Avatar 210 may interact with or mirror the movement of User 208 in real-time. In some embodiments, tasks may be prompted by the Avatar 210. For example, the Avatar 210 may perform a certain physical therapy exercise or pose associated with such an exercise and prompt the User 208 to mimic the exercise or pose. In some embodiments, digital objects or environments may appear within Display 202 for the Avatar 210 to interact with, prompting User 208 to mirror the movement of the Avatar 210. In other embodiments, Avatar 210 mirrors the movement of User 208 after the user has completed a task. In certain embodiments, a visual indicator, e.g. a success notification, fireworks, balloons, etc., may appear to indicate that User 208 has successfully mimicked the Avatar 210 or completed an assigned task or exercise. In certain embodiments, a digital asset may be release upon recognition that the User 208 has completed a task or assigned exercise. A digital asset may be a coin or other digital item that may be accumulated and/or redeemed for other prizes or digital assets, e.g. videos, digital trading cards, etc. In some embodiments, a visual indicator may be displayed when the user has failed to complete the assigned task or exercise. For example, upon detection that an exercise has not be completed, an encouraging message may be displayed to User 208 or additional instructions may be given and/or displayed to encourage the User 208 to complete the exercise. In certain embodiments, an exercise or task may be determined to be completed when the User 208 is recognized as completing an assigned physical therapy pose, exercise, and/or task. In certain embodiments, movements of User 208 may be analyzed and interpreted (e.g. by Camera 304 and/or Processing Unit 306) to be within a threshold to be considered completed, e.g. according to a predetermined completion metric. For example, a physical therapy exercise may require User 208 to place both hands above their head. The acceptable threshold for this particular exercise may consider a user movement of one arm above their head as completed. In other situations, completion may be determined only when the both arms are raised to a satisfactory height. Acceptable thresholds to determine completion may vary according to ability of User 208. In some embodiments, acceptable thresholds may vary dynamically as the User 208 progresses in their therapy.

Avatar 210 may be customizable according to user preferences, and in some embodiments, can include appearance modifiers based on the physical characteristics of User 208. For example, Avatar 210 may be depicted in a wheelchair or missing a limb. In certain embodiments User 208 and Avatar 210 may be combined into a single character representative of User 208. In some embodiments, Avatar 210 may perform certain movements in response to detected movement by User 208. For example, User 208 may gesture for a "high-five" in which Avatar 210 may be depicted as reaching out to give the User 208 a "high-five." As another example, User 208 may gesture for a hug and the Avatar 210 may be depicted as giving a hug to User 208. It will be appreciated that additional gestures or recognized movements by a User 208 may be associated with corresponding actions to be depicted by Avatar 210 in response to the gesture being recognized.

In some embodiments, User 208 may complete assigned exercises by interacting with various digital objects or environments, and then the movements of User 208 will be replayed on the display along with layered digital content. For example, after a User 208 completes the assigned task of standing on one leg for 5 seconds, the video of User 208 standing on one leg might be replayed with digitally rendered flamingos also standing on one leg in a similar fashion to User 208. In another exemplary task, a User 208 may be instructed to run in place for a predetermined amount of time, and once the assigned task is completed the video of User 208 running is replayed with a new virtual background of running alongside Olympic athletes or a pack of cheetahs.

Figure 3:
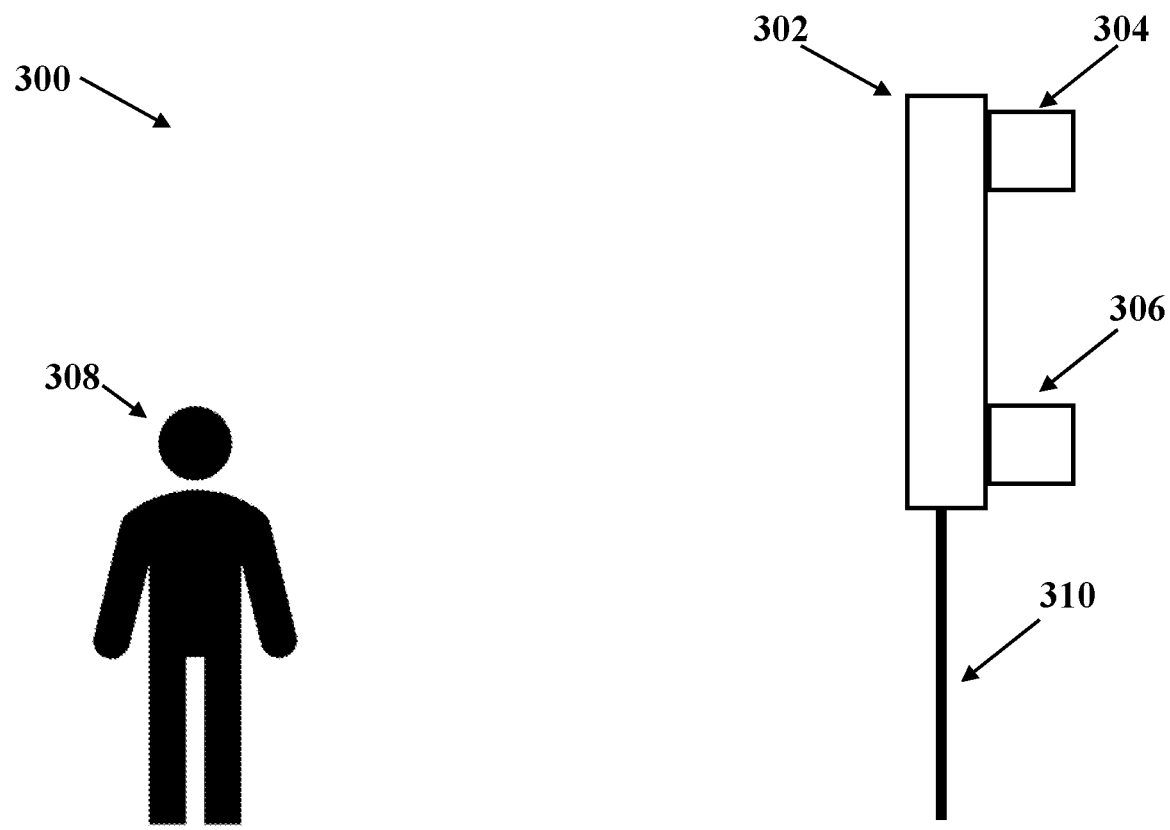
FIG. 3 shows another an exemplary augmented therapy system.

FIG. 3 shows an implementation of an exemplary augmented therapy system 300. A User 308 interacts with Display 302, Camera 304, and Processing Unit 306. It is further contemplated that the Display 302, Camera 304, and Processing Unit 306 may be supported by a stand 310. In some embodiments, stand 310 may be adjustable to accommodate User 308's field of view. In some embodiments, stand 310 may comprise a cart or other mobile support solution configured to couple Display 302, Camera 304, and Processing Unit 306 together for transport. It will be further appreciated that User 308 is a single user, however multiple users could be interacting with Display 300, Camera 302, and Processing Unit 306 in substantially the same way.

Figure 4:
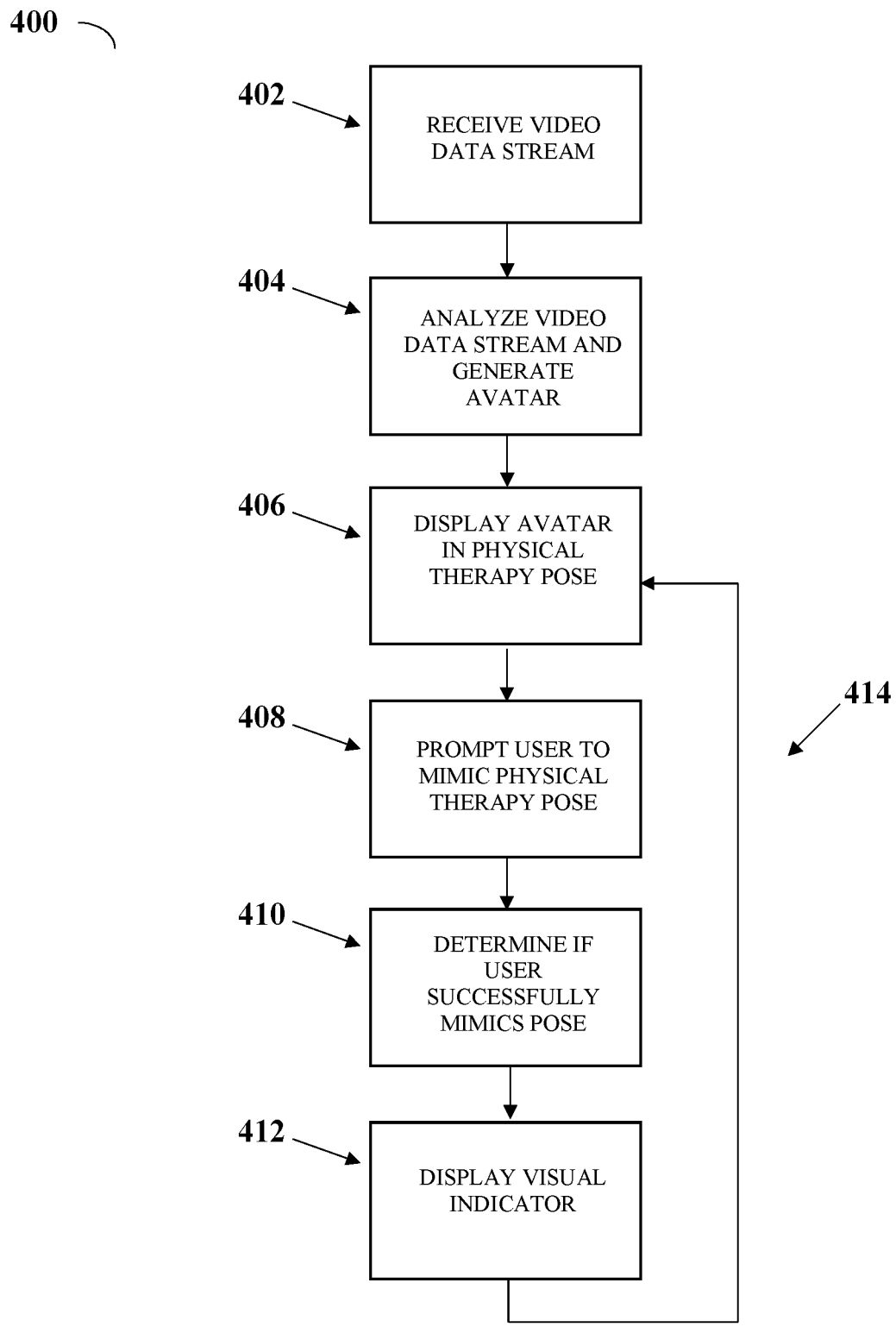
FIG. 4 shows an exemplary method for facilitating the completion of an interactive therapy exercise.

FIG. 4 shows steps according to an exemplary method 400 for facilitating the completion of an interactive physical therapy exercise. It will be appreciated that the illustrated method and associated steps may be performed in a different order, with illustrated steps omitted, with additional steps added, or with a combination of reordered, combined, omitted, or additional steps.

At step 402, a video data stream is received, e.g. from a first camera. At step 404, the video data stream may be analyzed, e.g. by a processing unit, to identify at least one user. Also at step 404, an avatar may be generated. In some embodiments, the avatar is based on the at least one user. At step 406, the avatar is displayed in at least one pose associated with a physical therapy exercise. In some embodiments, the avatar is displayed at a display proximate to the at least one user. At step 408, the user is prompted to mimic the physical therapy pose. At step 410, the video data stream may be analyzed to detect user movement and it is determined if the user has successfully mimicked the physical therapy pose. Upon the determination that the user has successfully mimicked the pose, a visual indicator associated with the successful performance of the poser may be displayed to the user at step 412. At step 414, more physical therapy exercises may be assigned and/or instructed by returning to step 406.

It is to be understood that the detailed description is intended to be illustrative, and not limiting to the embodiments described. Other embodiments will be apparent to those of skill in the art upon reading and understanding the above description. Moreover, in some instances, elements described with one embodiment may be readily adapted for use with other embodiments. Therefore, the methods and systems described herein are not limited to the specific details, the representative embodiments, or the illustrative examples shown and described. Accordingly, departures may be made from such details without departing from the spirit or scope of the general aspects of the present disclosure.

What is claimed is:

1. A method for facilitating the completion of an interactive physical therapy exercise, the method comprising:
    receiving a video data stream from a first camera;
    analyzing the video data stream to identify at least one user;
    generating an avatar, wherein the avatar is a digital character configured to perform movement associated with a physical therapy exercise;
    displaying, at a display, the avatar performing at least one movement associated with the physical therapy exercise, wherein the display is in a field of view of the at least one user;
    prompting the at least one user to mimic the at least one movement;
    analyzing the video data stream to detect movement of the at least one user;
    automatically determining if the at least one user successfully mimics the at least one movement based on the detected movement and a completion metric associated with the at least one movement, wherein the completion metric is characterized by the at least one user and dynamically adjusted based upon progress of a therapy associated with the physical therapy exercise; and
    displaying, at the display, a visual indicator when the at least one user successfully mimics the at least one movement, wherein the visual indicator is a graphical element indicative of completion of a portion of the physical therapy exercise.

2. The method according to claim 1, wherein the avatar is generated according to at least one physical characteristic of the at least one identified user.

3. The method according to claim 1, further comprising collecting a plurality of datapoints associated with the detected movement of the at least one user.

4. The method according to claim 3, wherein the plurality of datapoints are collected using a laser grid array.

5. The method according to claim 3, wherein the plurality of datapoints are associated with the completion metric.

6. The method according to claim 1, further comprising displaying a second visual indicator when the at least one user fails to successfully mimic the at least one movement.

7. The method according to claim 1, further comprising receiving a second video data stream from a second camera and analyzing the video data stream and the second video data stream to detect movement of the at least one user.

8. The method according to claim 1, wherein the visual indicator is an animated graphical element.

9. A system for facilitating the completion of an interactive physical therapy exercise, the system comprising:
    a first camera configured to capture a video data stream; and,
    a processing unit configured to:
        receive the video data stream from the first camera;
        analyze the video data stream to identify at least one user;
        generate an avatar, wherein the avatar is a digital character configured to perform movement associated with a physical therapy exercise;
        display the avatar performing at least one movement associated with the physical therapy exercise;
        generate a prompt to the at least one user to mimic the at least one movement;
        analyze the video data stream to detect movement of the at least one user;
        determine if the at least one user successfully mimics the at least one movement based on the detected movement and a completion metric associated with the at least one movement, wherein the completion metric is characterized by the at least one user and dynamically adjusted based upon progress of a therapy associated with the physical therapy exercise; and
        generate a visual indicator when the at least one user successfully mimics the at least one movement, wherein the visual indicator is a graphical element indicative of completion of a portion of the physical therapy exercise.

10. The system according to claim 9, further comprising: a display configured to display the avatar, prompt, and visual indicator generated by the processing unit.

11. The system according to claim 9, wherein the avatar is generated according to at least one physical characteristic of the at least one identified user.

12. The system according to claim 9, wherein the processing unit is further configured to collect a plurality of datapoints associated with the detected movement of the at least one user.

13. The system according to claim 12, wherein the plurality of datapoints are collected using a laser grid array.

14. The system according to claim 12, wherein the plurality of datapoints are associated with the completion metric.

15. The system according to claim 9, further comprising a second camera configured to capture a second video data stream.

16. The system according to claim 15, wherein the processing unit is configured to analyze the video data stream captured from the first camera and the second video data stream captured from the second camera to detect movement of the at least one user.

17. The system according to claim 9, further comprising generating a second visual indicator when the at least one user fails to successfully mimic the at least one movement.

18. A method for facilitating the completion of an interactive physical therapy exercise, the method comprising:
    receiving a video data stream from a first camera;
    analyzing the video data stream to identify at least one user;
    displaying an image of the at least one user based on the video data stream;
    generating at least one digital object, wherein the at least one digital object is configured to be manipulated by the at least one user through movement of the user;
    displaying the at least one digital object and the image of the at least one user within a field of view of the at least one user;
    prompting the at least one user to perform an interaction with the digital object;
    analyzing the video data stream to detect movement of the at least one user to determine if the at least one user has performed the interaction according to a completion metric associated with the interaction, wherein the completion metric is characterized by the at least one user and dynamically adjusted based upon progress of a therapy associated with the physical therapy exercise;
    responsive to an automatic determination that the at least one user has performed the interaction, generating a visual indicator, wherein the visual indicator is a graphical element indicative of completion of the interaction; and
    displaying the visual indicator when the at least one user successfully performs the interaction with the digital object.

19. The method according to claim 18, wherein the image of the at least one user comprises at least one digital overlay.

20. The method according to claim 18, further comprising collecting a plurality of datapoints associated with the detected movement of the at least one user.

* * * * *